US006028176A

United States Patent [19]

Greve et al.

[11] Patent Number: 6,028,176

[45] **Date of Patent: *Feb. 22, 2000**

[54] HIGH-AFFINITY INTERLEUKIN-4 MUTEINS

[75] Inventors: Jeffrey M. Greve, Berkeley; Armen B. Shanafelt, Moraga; Steven Roczniak, Lafayette, all of Calif.

[73] Assignee: Bayer Corporation, Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/897,020

[22] Filed: Jul. 18, 1997

Related U.S. Application Data

[60] Provisional application No. 60/022,537, Jul. 19, 1996.

[51] Int. Cl.[7] .......................... C07K 14/54; A61K 38/20

[52] U.S. Cl. .......................... 530/351; 530/402; 930/141; 424/85.2

[58] Field of Search .................................... 530/351, 402; 424/85.2; 930/141

[56] References Cited

U.S. PATENT DOCUMENTS

| | | | |
|---|---|---|---|
| 5,017,691 | 5/1991 | Lee et al. | 535/351 |
| 5,506,107 | 4/1996 | Cunningham et al. | 435/721 |

FOREIGN PATENT DOCUMENTS

| | | | |
|---|---|---|---|
| 0230107 | 7/1987 | European Pat. Off. . | |
| 8702990 | 5/1987 | WIPO | C07K 15/00 |
| 8804667 | 6/1988 | WIPO | C07K 13/00 |
| 9221029 | 11/1992 | WIPO | C07K 13/00 |
| 9321308 | 10/1993 | WIPO | C12N 13/00 |
| 9400491 | 1/1994 | WIPO | C07K 13/00 |
| 9527052 | 10/1995 | WIPO | C12N 15/00 |
| 9527732 | 10/1995 | WIPO | C07K 14/00 |
| 9604306 | 2/1996 | WIPO | C07K 14/55 |
| 9604388 | 2/1996 | WIPO | C12N 15/62 |
| 9609323 | 3/1996 | WIPO | C07K 14/54 |

OTHER PUBLICATIONS

Hilton, D., et al., Cloning and characterization of a binding subunit of the interleukin–13 receptor that is also a component of the interleukin–4 receptor, PNAS–USA 93: 497–501 (1996).

Obiri, N., et al., Receptor for Interleukin 13, The Journal of Biological Chemistry—vol. 270, No. 15 (1995), pp. 8797–8804.

Matthews, D., et al., Function of the interleukin–2(IL–2) receptor γ–chain in biologic responses of X–linked severe combined immunodeficient B cells to IL–2, IL–4, IL–13, and IL–15, Blood 85(1):38–42 (1995).

Walter, et al., Crystal structure of a complex between interferon–γ and its soluble high–affinity receptor, Nature—vol. 376 (1995), pp. 230–235.

Kondo, M., et al., Sharing of the interleukin–2 (IL–2) receptor γ chain between receptors for IL–2 and IL–4, Science—vol. 262 (1993), pp. 1874–1877.

Russell, S., et al., Interleukin–2 receptor γ chain: a functional component of the interleukin–4 receptor, Science—vol. 262 (1993), pp. 1880–1883.

Economides, A., et al., Designer cytokines: targeting actions to cells of choice, Science—vol. 270 (1995), pp. 1351–1353.

Wlodawer, A., et al., Hematopoietic cytokines: similarities and differences in the structures, with implications for receptor binding, Protein Science vol. 2 (1993), pp. 1373–1382.

Kaushansky, K., et al., Hematopoietic growth factors: understanding functional diversity in structural terms, Blood—vol. 82, No. 11 (1993), pp. 3229–3240.

Kruse, N., et al., Two distinct functional sites of human interleukin–4 are identified by variants impaired in either receptor binding or receptor activation, The EMBO Journal—vol. 12, No. 13 (1993), pp. 5121–5129.

Kruse, N., et al., Conversion of human interleukin–4 into a high affinity antagonist by a single amino acid replacement, the EMBO Journal—vol. 11, No. 9 (1992), pp. 3237–3244.

Zurawski, S., et al., Receptors for interleukin–13 and interleukin–4 are complex and share a novel component that functions in signal transduction, The EMBO Journal—vol. 12, No. 7 (1993) pp. 2663–2670.

Aversa, G., et al., An interleukin–4 (IL–4) mutant protein inhibits both IL–4 or IL–13 induced human immunoglobulin G4 (IgG4) and IgE Synthesis and B cell proliferation: support for a common component shared by IL–4 and IL–13 receptors, J. Exp. Med. 178:2213–2218 (1993).

Maher, D.W., et al., Human interleukin–4: an immunomodulator with potential therapeutic applications, Progress in Growth Factor Research—vol. 3 (1991), pp. 43–56.

Liblau, R., et al., Th1 and Th2 CD4+ T cells in the pathogenesis of organ–specific autoimmune diseases, Immunology Today—vol. 16, No. 1 (1995), pp. 34–38.

Margolin, K., et al., Phase II studies of recombinant human interleukin–4 in advanced renal cancer and malignant melanoma, Journal of Immunotherapy—vol. 15, pp. 147–153 (1994).

(List continued on next page.)

*Primary Examiner*—Garnette D. Draper
*Attorney, Agent, or Firm*—Huw R. Jones

[57] ABSTRACT

This invention is directed to recombinant human IL-4 muteins numbered in accordance with wild-type IL-4 wherein the muteins comprise at least one amino acid substitution selected from the group consisting of substitutions at positions 13, 16, 81 and 89 of the wild-type IL-4, whereby the mutein binds to the IL-4Rα receptor with at least greater affinity than native IL-4. The invention is further directed to recombinant human IL-4 antagonist muteins numbered in accordance with wild-type IL-4 wherein the muteins comprise substitutions R121D and Y124D in the D-helix of said wild-type IL-4; and at least one amino acid substitution selected from the group consisting of substitutions at positions 13, 16, 81 and 89 of said wild-type IL-4, whereby the mutein binds to the IL-4Rα receptor with at least greater affinity than native IL-4. The invention is also directed to pharmaceutical compositions comprising individual muteins in combination with pharmaceutically acceptable carriers.

21 Claims, 6 Drawing Sheets

OTHER PUBLICATIONS

Schnyder, B., et al., Interleukin–4 (IL–4) and IL–13 bind to a shared heterodimeric complex on endothelial cells mediating vascular cell adhesion molecule–1 induction in the absence of the common γ chain, Blood—vol. 87, No. 10 (1996), pp. 4286–4295.

Callard, R., et al., IL–4 and IL–13 receptors: are they one and the same?, Immunology Today—vol. 17, No. 3 (1996), pp. 108–110.

Morrison, B., et al., A receptor binding domain of mouse interleukin–4 defined by a solid–phase binding assay and in vitro mutagenesis, The Journal of Biological Chemistry—vol. 267, No. 17 (1992), pp. 11957–11963.

Olins, P., et al., Saturation mutagenesis of human interleukin–3, The Journal of Biological Chemistry—vol. 270, No. 40 (1995), pp. 23754–23760.

Lopez, A., et al., A human interleukin–3 analog with increased biological and binding activities, PNAS (USA)—vol. 89 (1992), pp. 11842–11846.

Lewis, C., et al., Use of a novel mutagenesis strategy, optimized residue substitution, to decrease the off–rate of an anti–gp120 antibody, Molecular Immunology—vol. 32, No. 14 (1995), pp. 1065–1072.

Savino, R., et al., Saturation mutagenesis of the human interleukin–6 receptor–binding site: implications for its three–dimensional structure, PNAS (USA)—vol. 90 (1993), pp. 4067–4071.

Savino, R., et al., Rational design of a receptor super–antagonist of human interleukin–6, The EMBO Journal—vol. 13, No. 24 (1994), pp. 5863–5870.

Lakkis, F., et al., Phe496 and Leu497 are essential for receptor binding and cytotoxic action of the murine interleukin–4 receptor targeted fusion toxin $DAB_{389}$–mIL–4, Protein Engineering—vol. 5, No. 3 (1992), pp. 241–248.

Powrie, F., et al., Cytokine regulation of T–cell function: potential for therapeutic intervention, Immunology Today—vol. 14, No. 6 (1993), pp. 270–274.

Racke, M.K., et al., Cytokine–induced immune deviation as a therapy for inflammatory autoimmune disease, J Exp. Med. (USA)—vol. 180, No. 5 (1994), pp. 1961–1966—Abstract.

Duschl, A., et al., "Antagonistic mutant proteins of interleukin–4" Behring Institute Mitteilungen—No. 6 (1995), pp. 87–94.

Morrison et al *JBC* 267 (17) 1992, p. 11957–63.

Muller et al *J. Mol Biol* 1995, v247, p. 360–72.

sIL-4Rα-STX (SEQ ID NO:7)

Met Lys Val Leu Gln Glu Pro Thr Cys Val Ser Asp Tyr Met Ser
1 5 10 15

Ile Ser Thr Cys Glu Trp Lys Met Asn Gly Pro Thr Asn Cys Ser
20 25 30

Thr Glu Leu Arg Leu Gly Ala Gly Cys Val Cys His Leu Leu Met
35 40 45

Asp Asp Val Val Ser Ala Asp Asn Tyr Thr Leu Asp Leu Trp Ala
50 55 60

Gly Gln Gln Leu Leu Trp Lys Gly Ser Phe Lys Pro Ser Glu His
65 70 75

Val Lys Pro Arg Ala Pro Gly Asn Leu Thr Val His Thr Asn Val
80 85 90

Ser Asp Thr Leu Leu Leu Thr Trp Ser Asn Pro Tyr Pro Pro Asp
95 100 105

Asn Tyr Leu Tyr Asn His Leu Thr Tyr Ala Val Asn Ile Trp Ser
110 115 120

Glu Asn Asp Pro Ala Asp Phe Arg Ile Tyr Asn Val Thr Tyr Leu
125 130 135

Glu Pro Ser Leu Arg Ile Ala Ala Ser Thr Leu Lys Ser Gly Ile
140 145 150

Ser Tyr Arg Ala Arg Val Arg Ala Trp Ala Gln Cys Tyr Asn Thr
155 160 165

Thr Trp Ser Glu Trp Ser Pro Ser Thr Lys Trp His Asn Ser Tyr
170 175 180

Arg Glu Pro Phe Glu Gln His Ser Ala Trp Arg His Pro Gln Phe
185 190 195

Gly Gly

FIG. 4

T13D-IL4 (SEQ ID NO: 8)

```
       ATGGGTCTCACCTCCCAACTGCTTCCCCCTCTGTTCTTCCTGCTAGCATGTGCCGGCAAC
     1 ------+---------+---------+---------+---------+---------+--- 60
       TACCCAGAGTGGAGGGTTGACGAAGGGGGAGACAAGAAGGACGATCGTACACGGCCGTTG

a:     MetGlyLeuThrSerGlnLeuLeuProProLeuPhePheLeuLeuAlaCysAlaGlyAsn  -

       TTTGTCCACGGACACAAGTGCGATATCACCTTACAGGAGATCATCAAAGATTTGAACAGC
    61 ------+---------+---------+---------+---------+---------+--- 120
       AAACAGGTGCCTGTGTTCACGCTATAGTGGAATGTCCTCTAGTAGTTTCTAAACTTGTCG

a:     PheValHisGlyHisLysCysAspIleThrLeuGlnGluIleIleLysAspLeuAsnSer  -

       CTCACAGAGCAGAAGACTCTGTGCACCGAGTTGACCGTAACAGACATCTTTGCTGCCTCC
   121 ------+---------+---------+---------+---------+---------+--- 180
       GAGTGTCTCGTCTTCTGAGACACGTGGCTCAACTGGCATTGTCTGTAGAAACGACGGAGG

a:     LeuThrGluGlnLysThrLeuCysThrGluLeuThrValThrAspIlePheAlaAlaSer  -

       AAGAACACAACTGAGAAGGAAACCTTCTGCAGGGCTGCGACTGTGCTCCGGCAGTTCTAC
   181 ------+---------+---------+---------+---------+---------+--- 240
       TTCTTGTGTTGACTCTTCCTTTGGAAGACGTCCCGACGCTGACACGAGGCCGTCAAGATG

a:     LysAsnThrThrGluLysGluThrPheCysArgAlaAlaThrValLeuArgGlnPheTyr  -

       AGCCACCATGAGAAGGACACTCGCTGCCTGGGTGCGACTGCACAGCAGTTCCACAGGCAC
   241 ------+---------+---------+---------+---------+---------+--- 300
       TCGGTGGTACTCTTCCTGTGAGCGACGGACCCACGCTGACGTGTCGTCAAGGTGTCCGTG

a:     SerHisHisGluLysAspThrArgCysLeuGlyAlaThrAlaGlnGlnPheHisArgHis  -

       AAGCAGCTGATCCGATTCCTGAAACGGCTCGACAGGAACCTCTGGGGCCTGGCGGGCTTG
   301 ------+---------+---------+---------+---------+---------+--- 360
       TTCGTCGACTAGGCTAAGGACTTTGCCGAGCTGTCCTTGGAGACCCCGGACCGCCCGAAC

a:     LysGlnLeuIleArgPheLeuLysArgLeuAspArgAsnLeuTrpGlyLeuAlaGlyLeu  -

       AATTCCTGTCCTGTGAAGGAAGCCAACCAGAGTACGTTGGAAAACTTCTTGGAAAGGCTA
   361 ------+---------+---------+---------+---------+---------+--- 420
       TTAAGGACAGGACACTTCCTTCGGTTGGTCTCATGCAACCTTTTGAAGAACCTTTCCGAT

a:     AsnSerCysProValLysGluAlaAsnGlnSerThrLeuGluAsnPheLeuGluArgLeu  -

       AAGACGATCATGAGAGAGAAATATTCAAAGTGTTCGAGCTAG
   421 ------+---------+---------+---------+----- 464
       TTCTGCTAGTACTCTCTCTTTATAAGTTTCACAAGCTCGATC

a:     LysThrIleMetArgGluLysTyrSerLysCysSerSerEnd  -
```

FIG. 5

T13D-IL4[R121D/Y124D] (SEQ ID NO: 9)

```
    ATGGGTCTCACCTCCCAACTGCTTCCCCCTCTGTTCTTCCTGCTAGCATGTGCCGGCAAC
  1 ------+---------+---------+---------+---------+---------+--- 60
    TACCCAGAGTGGAGGGTTGACGAAGGGGGAGACAAGAAGGACGATCGTACACGGCCGTTG

a:  MetGlyLeuThrSerGlnLeuLeuProProLeuPhePheLeuLeuAlaCysAlaGlyAsn -

    TTTGTCCACGGACACAAGTGCGATATCACCTTACAGGAGATCATCAAAGATTTGAACAGC
 61 ------+---------+---------+---------+---------+---------+--- 120
    AAACAGGTGCCTGTGTTCACGCTATAGTGGAATGTCCTCTAGTAGTTTCTAAACTTGTCG

a:  PheValHisGlyHisLysCysAspIleThrLeuGlnGluIleIleLysAspLeuAsnSer -

    CTCACAGAGCAGAAGACTCTGTGCACCGAGTTGACCGTAACAGACATCTTTGCTGCCTCC
121 ------+---------+---------+---------+---------+---------+--- 180
    GAGTGTCTCGTCTTCTGAGACACGTGGCTCAACTGGCATTGTCTGTAGAAACGACGGAGG

a:  LeuThrGluGlnLysThrLeuCysThrGluLeuThrValThrAspIlePheAlaAlaSer -

    AAGAACACAACTGAGAAGGAAACCTTCTGCAGGGCTGCGACTGTGCTCCGGCAGTTCTAC
181 ------+---------+---------+---------+---------+---------+--- 240
    TTCTTGTGTTGACTCTTCCTTTGGAAGACGTCCCGACGCTGACACGAGGCCGTCAAGATG

a:  LysAsnThrThrGluLysGluThrPheCysArgAlaAlaThrValLeuArgGlnPheTyr -

    AGCCACCATGAGAAGGACACTCGCTGCCTGGGTGCGACTGCACAGCAGTTCCACAGGCAC
241 ------+---------+---------+---------+---------+---------+--- 300
    TCGGTGGTACTCTTCCTGTGAGCGACGGACCCACGCTGACGTGTCGTCAAGGTGTCCGTG

a:  SerHisHisGluLysAspThrArgCysLeuGlyAlaThrAlaGlnGlnPheHisArgHis -

    AAGCAGCTGATCCGATTCCTGAAACGGCTCGACAGGAACCTCTGGGGCCTGGCGGGCTTG
301 ------+---------+---------+---------+---------+---------+--- 360
    TTCGTCGACTAGGCTAAGGACTTTGCCGAGCTGTCCTTGGAGACCCCGGACCGCCCGAAC

a:  LysGlnLeuIleArgPheLeuLysArgLeuAspArgAsnLeuTrpGlyLeuAlaGlyLeu -

    AATTCCTGTCCTGTGAAGGAAGCCAACCAGAGTACGTTGGAAAACTTCTTGGAAAGGCTA
361 ------+---------+---------+---------+---------+---------+--- 420
    TTAAGGACAGGACACTTCCTTCGGTTGGTCTCATGCAACCTTTTGAAGAACCTTTCCGAT

a:  AsnSerCysProValLysGluAlaAsnGlnSerThrLeuGluAsnPheLeuGluArgLeu -

    AAGACGATCATGGACGAGAAAGACTCAAAGTGTTCGAGCTAG
421 ---+---------+---------+---------+-------- 464
    TTCTGCTAGTACCTGCTCTTTCTGAGTTTCACAAGCTCGATC

a:  LysThrIleMetAspGluLysAspSerLysCysSerSerEnd -
```

FIG. 6

HIGH-AFFINITY INTERLEUKIN-4 MUTEINS

This application claims the benefit of U.S. Provisional Pat. Application No. 60/022,537, filed Jul. 19, 1996, now abandoned.

BACKGROUND

1. Field of the Invention

The invention is generally related to the fields of pharmacology and immunology. More specifically, the invention is directed to novel variants of the cytokine family, and in particular human Interleukin 4 (IL-4).

2. Description of Related Art

Interleukin-4 is a 15 kDa glycoprotein secreted by activated T cells, (Howard et al., *J. Exp. Med.* 155:914 (1982)), mast cells (Brown et al., *Cell* 50:809(1987)) and basophils (Seder et al., *Proc. Natl. Acad. Sci. USA* 88:2835(1991)) which regulates a wide spectrum of cellular functions in hematopoietic and nonhematopoetic cells. The sequence of IL-4 is disclosed in U.S. Pat. No. 5,017,691. Interleukin 4 (IL-4) is a pleiotropic cytokine, having activities on cells of the immune system, endothelium, and those of fibroblastic nature. Reported in vitro effects of IL-4 administration include proliferation of T and B cells, immunoglobulin class switching in B cells, stimulation of production of cellular surface adhesion molecules in endothelial cells, and stimulation of IL-6 release. In T cells, IL-4 stimulates T cell proliferation after preactivation with mitogens and down regulates IFN-γ production. In monocytes, IL-4 induces class II MHC molecule expression, release of lipopolysaccharide-induced tPA, and CD23 expression. In Endothelial cells (EC), IL-4 induces expression of VCAM-1 and IL-6 release. IL-4 decreases ICAM-1 expression. Mahér, D W, et al., Human Interleukin-4: An Immunomodulator with Potential Therapeutic Applications, *Progress in Growth Factor Research,* 3:43–56 (1991).

Because of its ability to stimulate proliferation of T cells activated by exposure to IL-2, IL-4 therapy has been pursued. For instance, IL-4 has demonstrated anti-neoplastic activity in animal models of renal carcinomas, and has induced tumor regression in mice (Bosco, M., et al., Low Doses of IL-4 Injected Perilymphatically in Tumor-bearing Mice Inhibit the Growth of Poorly and Apparently Nonimmunogenic Tumors and Induce a Tumor Specific Immune Memory, *J. Immunol.* 145:3136–43 (1990)). However, its toxicity limits the dosage in humans (Margolin, K., et al. Phase II Studies of Human Recombinant Interleukin-4 in Advanced Renal Cancer and Malignant Melanoma, *J. Immunotherapy* 15:147–153 (1994).

The general structure and function of IL-4 and related monomeric ligands containing 4 antiparallel a-helical domains (A–D) is now known. The three-dimensional structure of IL-4 has been solved (Powers et al., *Science* 256:1673) (1992). The protein contains 4 left hand a-helices and two b-sheets.

The IL-4 receptor consists of at least two chains. The first IL-4R chain, IL-4Rα, shares significant homology to the b chain of the IL-2R and other members of the growth factor receptor superfamily (Ldzerda et al. *J. Exp. Med.* 171:861 (1990)). A second IL-4R chain has been identified, the chain of the IL-2R, also known as the 'common chain', $\gamma_c$ (Russell et al., *Science* 262:1877(1993). The two binding sites are likely involved in a sequential, two-binding event that results in a ternary 1:1:1 complex. The region of IL-4 likely responsible for binding with IL-4Rα is thought to be located on either or both of helices A and C, while the region interactive with $g_c$ is thought to be located on helix D. Present theory holds that the first binding event involves the ligand contacting IL-4Rα, the primary binding component. No cellular signaling activity is associated with this event. The second binding event occurs when the IL-4/IL-4Rα complex recruits a second chain, gc. After this second binding event, signaling occurs and cellular activity is established. Antagonism of wild-type IL-4 is found when binding interactions mediated by the second region (necessary for cellular activity) are diminished or eliminated, while retaining binding to IL-4Rα. Agonism occurs when a candidate ligand constructively interacts, via the first and second regions, to both receptor components.

Antagonists of IL-4 have been reported in the literature. Mutants of IL-4 that function as antagonists include the IL-4 antagonist mutein IL-4/Y124D (Kruse, N., Tony, H. P., Sebald, W., Conversion of human interleukin-4 into a high affinity antagonist by a single amino acid replacement, *Embo J.* 11:3237–44, 1992) and a double mutein IL-4[R121D/Y124D] (Tony, H., et al., Design of Human Interleukin-4 Antagonists in Inhibiting Interleukin-4-dependent and Interleukin-13-dependent responses in T-cells and B-cells with high efficiency, *Eur. J. Biochem.* 225:659–664 (1994)). The single mutein is a substitution of tyrosine by aspartic acid at position 124 in the D-helix. The double mutein is a substitution of Arginine by Aspartic Acid at position 121, and of tyrosine by aspartic acid at position 124 in the D-helix. Variations in this section of the D helix positively correlate with changes in interactions at the second binding region.

Mutant variants of IL-4 demonstrating agonism or antagonism of wild-type IL-4 may be useful for treating conditions associated with one of the pleiotropic effects of IL-4. For instance, antagonists of IL-4 would be useful in treating conditions exacerbated by IL-4 production such as asthma, allergy, or other inflammatory response-related conditions. Agonists of IL-4 may be useful for treating conditions wherein the presence of IL-4 is associated with the amelioration or attenuation of a disease, for example, an autoimmune disease such as Rheumatoid Arthritis, Multiple Sclerosis, Insulin-dependent Diabetes Mellitus, etc. These autoimmune diseases are characterized by a polarization in production of the T helper cell populations, types 1 and 2 (Th1, Th2). Naive CD4+ T cells differentiate into Th1 or Th2 subsets, depending on the cytokine present during stimulation. An IL-4 agonist would ideally shift production to the T-helper cell desired, i.e., towards Th2, thereby having a therapeutic effect.

PCT/US93/03613 discloses an IL-4 variant having a Phe-Leu or Tyr-Leu sequence in a alpha-helical domain and a negatively-charged amino acid within two amino acids immediately upstream or downstream from the Phe-Leu or Tyr-Leu sequence, the variant having an increased affinity for the IL-4 receptor by virtue of a neutral amino acid substituted for the negatively-charged amino acid. It also discloses that the specific substitution of Trp-Leu or Phe-Leu within an a-helix of IL-4 within 2-residues of a negatively charged residue results in improved affinity. The variant is an IL-4 fusion protein (with diphtheria toxin).

SUMMARY OF THE INVENTION

The invention is directed to a recombinant human IL-4 mutein numbered in accordance with wild-type IL-4 wherein the mutein comprises at least one amino acid substitution in the binding surface of either the A- or C-alpha helices of the wild-type IL-4 whereby the mutein binds to the IL-4Rα receptor with at least greater affinity than native IL-4. The substitution is preferably selected from the group of positions consisting of, in the A-helix, positions 13 and 16, and in the C-helix, positions 81 and 89. A most preferred embodiment is the recombinant human IL-4 mutein wherein the substitution at position 13 is Thr to Asp. Pharmaceutical compositions, amino acid and polynucleotide sequences encoding the muteins, transformed host cells, antibodies to the muteins, and methods of treatment are also described.

The invention is also directed to an assay for determining the ability of a mutein to bind to a receptor, comprising the steps of: first introducing into a FlashPlate" coated with streptavidin the binding portion of a receptor chain, the binding portion of a receptor chain having a peptide tag capable of being bound by streptavidin; secondly introducing into the FlashPlate a radiolabelled native ligand having an affinity for the binding portion of a receptor chain; thirdly introducing into the FlashPlate a mutein ligand having an affinity for the binding portion of a receptor chain; the measuring of the amount of signal given off by the FlashPlate after allowing for equilibration; and lastly calculating the relative affinity of the mutein ligand versus the native ligand. In a preferred mode, the method uses the receptor chain IL-4Rα.

The invention is also directed to a recombinant human IL-4 antagonist mutein numbered in accordance with wild-type IL-4 wherein the mutein comprises: (a) substitutions R121D and Y124D in the D-helix of the wild-type IL-4; and (b) at least one amino acid substitution in the binding surface of either the A- or C-alpha helices of the wild-type IL-4 whereby the mutein binds to the IL-4Rα receptor with at least greater affinity than native IL-4. The substitution is preferably selected from the group of positions consisting of, in the A-helix, positions 13 and 16, and in the C-helix, positions 81 and 89. A most preferred embodiment is the recombinant human IL-4 antagonist mutein wherein the substitution at position 13 is Thr to Asp. Pharmaceutical compositions, amino acid and polynucleotide sequences encoding the muteins, transformed host cells, antibodies to the muteins, and methods of treatment are also described.

BRIEF DESCRIPTION OF THE FIGURES

FIG. 4 is the amino acid sequence listing of sIL-4Rα-STX.

FIG. 5 is a composite sequence listing of the T13D-IL-4 mutein.

FIG. 6 is a composite sequence listing of the T13D-IL-4 [R121D/Y124D] mutein.

DESCRIPTION OF THE PREFERRED EMBODIMENTS

Figure 1:
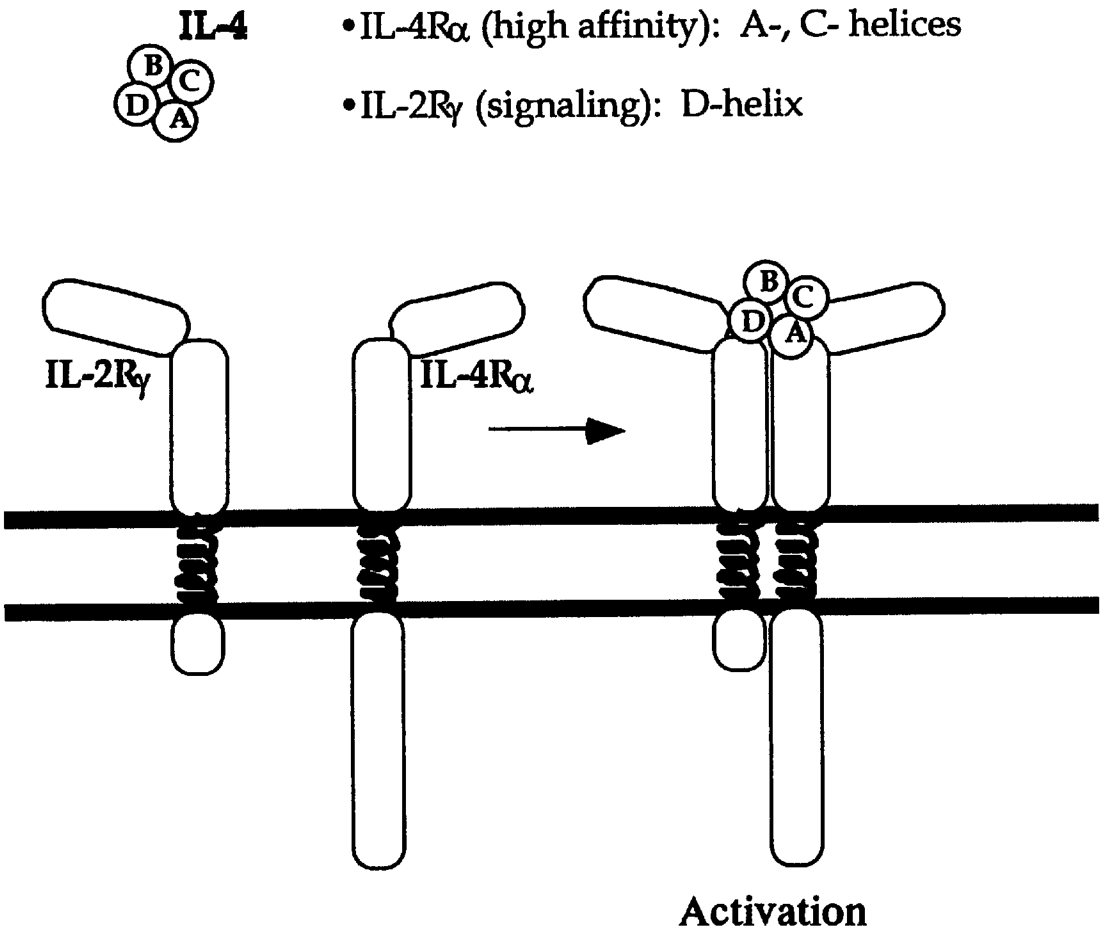
FIG. 1 is a schematic view of the ligand/receptor architecture for IL-4. IL-4 is a four-helix bundle protein, and is shown here in an 'end on' view of the four helices (A, B, C, and D, from the N- to the C-terminus, respectively). The primary binding component of the IL-4 receptor is IL-4Rα, which interacts with IL-4 ligand via the A- and C-helices of IL-4. Formation of the ternary complex IL-4/IL-4Rα/IL-4Rγ induces signaling in the target cell.

Described herein are novel muteins and a mechanism for deriving novel IL-4 muteins having higher affinities for wt IL-4 receptor.

As used herein, "wild type IL-4" or "wtIL-4" means human Interleukin-4, whether native or recombinant, having the 129 normally occurring amino acid sequence of native human IL-4, as disclosed in U.S. Pat. No. 5,017,691, incorporated herein by reference.

As used herein, "IL-4 mutein" means a polypeptide wherein specific amino acid substitutions to the human mature interleukin-4 protein have been made, specifically to either the A or C-helices, and more preferably to those amino acids comprising their binding surfaces. The binding surface of the A helix is generally found to be from about amino acid position 5 to about 16; and in helix C, from about position 77 to about 89. These changes to either helix increase the affinity of the resulting mutein for IL-4Rα, which mutein may be either an agonist or an antagonist of wt IL-4, depending upon the final nature of additional substitutions to the molecule.

As used herein, "IL-4 antagonist mutein" means a polypeptide wherein specific amino acid substitutions to the human mature interleukin-4 protein have been made. Specifically, the antagonist muteins presented herein contain at least three separate substitutions. The "IL-4[R121D/Y124D]" pair of substitutions are present in all antagonist muteins contained herein, and refer to a backbone pair of substitutions in the D-helix, R121D (Arg to Asp) and Y124D (Tyr to Asp). In addition, a third substitution has been introduced into the binding surfaces of either the A- or C-helix at a position that increases the binding affinity of the mutein to the receptor alpha chain. Aside from these changes, the most preferred IL-4 antagonist muteins have an amino acid sequence identical to wild type IL-4 at the other, non-substituted residues.

The IL-4 muteins of this invention may also be characterized by amino acid insertions, deletions, substitutions and modifications at one or more sites in or at the other residues of the native IL-4 polypeptide chain. In accordance with this invention any such insertions, deletions, substitutions and modifications should result in an IL-4 mutein that retains its IL-4-related activity.

We prefer conservative modifications and substitutions at other positions of IL-4 (i.e., those that have a minimal effect on the secondary or tertiary structure of the mutein). Such conservative substitutions include those described by Dayhoff in *The Atlas of Protein Sequence and Structure* 5 (1978), and by Argos in EMBO J., 8:779–785 (1989). For example, amino acids belonging to one of the following groups represent conservative changes:

ala, pro, gly, gln, asn, ser, thr;
cys, ser, tyr, thr;
val, ile, leu, met, ala, phe;
lys, arg, his;
phe, tyr, trp, his; and
asp, glu, tyr.

We also prefer modifications or substitutions that eliminate sites for intermolecular crosslinking or incorrect disulfide bond formation. For example, IL-4 is known to have six cys residues, at wild-type positions 3, 24, 46, 65, 99 and 127, one or more of which may be involved in cross-linking interactions. Substitutions should be selected so as to preserve the tertiary structure of the wild-type protein, as far as possible.

By "numbered in accordance with wild type IL-4" we mean identifying a chosen amino acid with reference to the position at which that amino acid normally occurs in wild type IL-4. Where insertions or deletions are made to the IL-4 antagonist mutein, one of skill in the art will appreciate that, for example, the Ser (S) normally occuring at position 125, when numbered in accordance with wild type IL-4, may be shifted in position in the mutein. However, the location of the shifted Ser (S) can be readily determined by inspection and correlation of the flanking amino acids with those flanking Ser in wild type IL-4.

The IL-4 muteins of the present invention can be produced by any suitable method known in the art. Such methods include constructing a DNA sequence encoding the IL-4 muteins of this invention and expressing those sequences in a suitably transformed host. This method will produce recombinant muteins of this invention. However, the muteins of this invention may also be produced, albeit less preferably, by chemical synthesis or a combination of chemical synthesis and recombinant DNA technology.

In one embodiment of a recombinant method for producing a mutein of this invention, a DNA sequence is constructed by isolating or synthesizing a DNA sequence encoding the wild type IL-4 and then changing the codon for threonine-13 to a codon for aspartatic acid by site-specific mutagenesis. This technique is well known. See, e.g., Mark et al., Site-specific Mutagenesis Of The Human Fibroblast Interferon Gene, *Proc. Natl. Acad. Sci. USA* 81:5662–66 (1984); U.S. Pat. No. 4,588,585, incorporated herein by reference.

Another method of constructing a DNA sequence encoding the IL-4 muteins of this invention would be chemical synthesis. For example, a gene which encodes the desired IL-4 mutein may be synthesized by chemical means using an oligonucleotide synthesizer. Such oligonucleotides are designed based on the amino acid sequence of the desired IL-4 mutein, and preferably selecting those codons that are favored in the host cell in which the recombinant mutein will be produced. In this regard, it is well recognized that the genetic code is degenerate—that an amino acid may be coded for by more than one codon. For example, Phe (F) is coded for by two codons, TTC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-4 mutein, there will be many degenerate DNA sequences that will code for that IL-4 mutein. For example, it will be appreciated that in addition to the preferred DNA sequence for mutein T13D-IL-4[R121D/Y124D] shown in SEQ ID NO: 9, there will be many degenerate DNA sequences that code for the IL-4 mutein shown. These degenerate DNA sequences are considered within the scope of this invention. Therefore, "degenerate variants thereof" in the context of this invention means all DNA sequences that code for a particular mutein.

The DNA sequence encoding the IL-4 mutein of this invention, whether prepared by site-directed mutagenesis, chemical synthesis or other methods, may or may not also include DNA sequences that encode a signal sequence. Such signal sequence, if present, should be one recognized by the cell chosen for expression of the IL-4 mutein. It may be prokaryotic, eukaryotic or a combination of the two. It may also be the signal sequence of native IL-4. The inclusion of a signal sequence depends on whether it is desired to secrete the IL-4 mutein from the recombinant cells in which it is made. If the chosen cells are prokaryotic, it generally is preferred that the DNA sequence not encode a signal sequence but include an N-terminal methionine to direct expression. If the chosen cells are eukaryotic, it generally is preferred that a signal sequence be encoded and most preferably that the wild-type IL-4 signal sequence be used.

Standard methods may be applied to synthesize a gene encoding an IL-4 mutein according to this invention. For example, the complete amino acid sequence may be used to construct a back-translated gene. A DNA oligomer containing a nucleotide sequence coding for IL-4 mutein may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site-directed mutagenesis or another method), the DNA sequences encoding an IL-4 mutein of this invention will be inserted into an expression vector and operatively linked to an expression control sequence appropriate for expression of the IL-4 mutein in the desired transformed host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E.coli*, including col El, pCRl, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2 m plasmid and derivatives thereof. Useful vectors for insect cells include pVL 941. We prefer pFastBac' 1 (GibcoBRL, Gaithersburg, Md.). Cate et al., Isolation Of The Bovine And Human Genes For Mullerian Inhibiting Substance And Expression Of The Human Gene In Animal Cells, *Cell,* 45:685–98 (1986).

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promotor of Baculovirus, and other sequences known to control the expression of genes of prokaryotic or eukaryotic cells or their viruses, and various combinations thereof.

Any suitable host may be used to produce the IL-4 muteins of this invention, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E. coli*, Pseudomonas, Bacillus, Streptomyces, fungi, yeast, insect cells such as *Spodoptera frugiperda* (*SF*9), animal cells such as Chinese hamster ovary (CHO) and mouse cells such as NS/O, African green monkey cells such as COS 1, COS 7, BSC 1, BSC 40, and BNT 10, and human cells, as well as plant cells in tissue culture. For animal cell expression, we prefer CHO cells and COS 7 cells in cultures and particularly the CHO cell line CHO (DHFR-).

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, preferred vectors for use in this invention include those that allow the DNA encoding the IL-4 muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, Construction Of A Modular Dihydrafolate Reductase cDNA Gene: Analysis Of Signals Utilized For Efficient Expression, *Mol. Cell. Biol.,* 2:1304–19 (1982)) or glutamine synthetase ("GS") amplification (see, e.g., U.S. Pat. No. 5,122,464 and European published application EPO338841).

In selecting an expression control sequence, a variety of factors should also be considered. These include, for example, the relative strength of the sequence, its controllability, and its compatibility with the actual DNA sequence encoding the IL-4 mutein of this invention, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters, one of skill in the art may select various vector/expression control sequence/host combinations that will express the desired DNA seguences on fermentation or in large scale animal culture, for example, using CHO cells or COS 7 cells.

The IL-4 muteins obtained according to the present invention may be glycosylated or unglycosylated depending on the host organism used to produce the mutein. If bacteria are chosen as the host then the IL-4 mutein produced will be unglycosylated. Eukaryotic cells, on the other hand, will glycosylate the IL-4 muteins, although perhaps not in the same way as native IL-4 is glycosylated.

The IL-4 mutein produced by the transformed host can be purified according to any suitable method. Various methods are known for purifying IL-4. See, e.g., U.S. Pat. Nos. 5,013,824 and 5,017,691; and WO9604306-A2. We prefer immunoaffinity purification. See, e.g., Okamura et al., Human Fibroblastoid Interferon: Immunosorbent Column Chromatography And N-Terminal Amino Acid Sequence, *Biochem.,* 19:3831–35 (1980).

The biological activity of the IL-4 muteins of this invention can be assayed by any suitable method known in the art. Such assays include antibody neutralization of antiviral activity, induction of protein kinase, oligoadenylate 2,5-A synthetase or phosphodiesterase activities, as described in EP-B1-41313. Such assays also include immunomodulatory assays (see, e.g., U.S. Pat. No. 4,753,795), growth inhibition assays, T cell proliferation, induction of IL-6, and induction of MCP-1 in endothelial cells and measurement of binding to cells that express interleukin-4 receptors. See also Spits H, Yssel H, Takebe Y, et al., Recombinant Interleukin-4 Promotes the Growth of Human T Cells, *J. Immunol.* 139:1142–47 (1987).

The IL-4 mutein of this invention will be administered at a dose approximately paralleling that or greater than employed in therapy with wild type native or recombinant IL-4. An effective amount of the IL-4 mutein is preferably administered. An "effective amount" means an amount capable of preventing or lessening the severity or spread of the condition or indication being treated. It will be apparent to those of skill in the art that the effective amount of IL-4 mutein will depend, inter alia, upon the disease, the dose, the administration schedule of the IL-4 mutein, whether the IL-4 mutein is administered alone or in conjunction with other therapeutic agents, the serum half-life of the composition, and the general health of the patient.

The IL-4 mutein is preferably administered in a composition including a pharmaceutically acceptable carrier. "Pharmaceutically acceptable carrier" means a carrier that does not cause any untoward effect in patients to whom it is administered. Such pharmaceutically acceptable carriers are well known in the art. We prefer 2% HSA/PBS at pH 7.0.

The IL-4 muteins of the present invention can be formulated into pharmaceutical compositions by well known methods. See, e.g., Remington's Pharmacautical Science by E. W. Martin, hereby incorporated by reference, describes suitable formulations. The pharmaceutical composition of the IL-4 mutein may be formulated in a variety of forms, including liquid, gel, lyophilized, or any other suitable form. The preferred form will depend upon the particular indication being treated and will be apparent to one of skill in the art.

The IL-4 mutein pharmaceutical composition may be administered orally, by aerosol, intravenously, intramuscularly, intraperitoneally, intradermally or subcutaneously or in any other acceptable manner. The preferred mode of administration will depend upon the particular indication being treated and will be apparent to one of skill in the art. The pharmaceutical composition of the IL-4 mutein may be administered in conjunction with other therapeutic agents. These agents may be incorporated as part of the same pharmaceutical composition or may be administered separately from the IL-4 mutein, either concurrently or in accordance with any other acceptable treatment schedule. In addition, the IL-4 mutein pharmaceutical composition may be used as an adjunct to other therapies.

Accordingly, this invention provides compositions and methods for treating immune disorders, cancers or tumors, abnormal cell growth, or for immunomodulation in any suitable animal, preferably a mammal, most preferably human. As previously noted in the Background section, IL-4 has many effects. Some of these are stimulation of T cell proliferation, T-helper cell differentiation, induction of human B-cell activation and proliferation, and lymphokine-directed immunoglobulin class switching of immunoglobulins. Effects on the lymphoid system include increasing the expression of MHC class II antigen (Noelle, R., et al., Increased Expression of Ia Antigens on resting B cells: a New Role for B Cell Growth Factor, *PNAS USA,* 81:6149–53 (1984), and CD 23 on B cells (Kikutani, H., et al., Molecular Structure of Human Lymphocyte Receptor for Immunoglobulin, *Cell* 47:657–61 (1986)). Thus, the biology of IL-4 suggests that it may have a significant role in the development of allergy and allergic inflammatory diseases including asthma. T-helper cell type 1 (Th1) and type 2 (Th2) are involved in the immune response. Stimulated Th2 cells secrete IL-4 and block Th1 progression. Any Th2-implicated disease is amenable to treatment by an IL-4 antagonist; likewise, any Th1-implicated disease is amenable to treatment by an IL-4 agonist.

Also contemplated is use of the DNA sequences encoding the IL-4 muteins of this invention in gene therapy applications. Gene therapy applications contemplated for IL-4 antagonists include treatment of those diseases in which IL-4 is expected to cause or exacerbate an existing clinical condition, such as an inflammation-related condition (asthma), or allergies. Agonist indications would include autoimmune diseases such as rheumatoid arthritis, multiple sclerosis, and insulin-dependent diabetes mellitus. These autoimmune diseases are characterized by a polarization in production of the T helper cell populations towards T helper type 1 (Th1).

Local delivery of IL-4 muteins, both agonist and antagonist, using gene therapy may provide the therapeutic agent to the target area while avoiding potential toxicity problems associated with non-specific administration of agonists. Both in vitro and in vivo gene therapy methodologies are contemplated. Several methods for transferring potentially therapeutic genes to defined cell papulations are known. See, e.g., Mulligan, The Basic Science Of Gene Therapy, *Science,* 260:926–31 (1993). These methods include:

1) Direct gene transfer. See, e.g., Wolff et al., Direct Gene transfer Into Mouse Muscle In Vivo, *Science,* 247:1465–68 (1990);

2) Liposome-mediated DNA transfer. See, e.g., Caplen at al., Liposome-mediated CFTR Gene Transfer To The Nasal Epithelium Of Patients With Cystic Fibrosis, *Nature Med.* 3:39–46 (1995); Crystal, The Gene As A Drug, *Nature Med.* 1:15–17 (1995); Gao and Huang, A Novel Cationic Liposome Reagent For Efficient Transfection Of Mammalian Cells, *Biochem. Biophys. Res. Comm.,* 179:280–85 (1991);

3) Retrovirus-mediated DNA transfer. See, e.g., Kay et al., In Vivo Gene Therapy Of Hemophilia B: Sustained Partial Correction In Factor IX-Deficient Dogs, *Science,* 262:117–19 (1993); Anderson, Human Gene Therapy, *Science,* 256:808–13 (1992);

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., The Use Of DNA Viruses As Vectors For Gene Therapy, *Gene Therapy,* 1:367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity.

Adenoviruses have the advantage that they have a broad host range, can infect quiescent or terminally differentiated cells, such as neurons or hepatocytes, and appear essentially non-oncogenic. See, e.g., Ali et al., supra, p. 367. Adenoviruses do not appear to integrate into the host genome. Because they exist extrachromosomally, the risk of insertional mutagenesis is greatly reduced. Ali et al., supra, p. 373.

Adeno-associated viruses exhibit similar advantages as adenoviral-based vectors. However, AAVs exhibit site-specific integration on human chromosome 19. Ali et al., supra, p. 377.

According to this embodiment, gene therapy with DNA encoding the IL-4 muteins of this invention is provided to a patient in need thereof, concurrent with, or immediately after diagnosis.

The skilled artisan will appreciate that any suitable gene therapy vector containing IL-4 mutein DNA may be used in accordance with this embodiment. The techniques for constructing such a vector are known. See, e.g., Ohno et al., supra, p. 784; Chang et al., supra, p. 522. Introduction of the IL-4 mutein DNA-containing vector to the target site may be accomplished using known techniques, e.g., as described in Ohno et al., supra, p. 784.

In order that this invention may be better understood, the following examples are set forth. These examples are for the purpose of illustration only, and are not to be construed as limiting the scope of the invention in any manner.

EXAMPLES

Generally

Alanine substitutions were introduced to the wild-type IL-4 sequence by site-directed mutagenesis at positions corresponding to residues predicted to be on the surface of the A- and C-helices of IL-4 (Smith L J; Redfield C; Boyd J; Lawrence G M; Edwards R G; Smith R A, and Dobson C M), Human interleukin 4. The solution structure of a four-helix bundle protein, *J. Mol. Biol.,* 224(4):899–904(1992). These residues are the most likely to mediate the interaction of IL-4 with IL-4Rα (FIG. 1); effects on the binding affinity of alanine substituted IL-4 muteins for IL-4Rα indicate that the substituted residue may be involved in the binding interaction. Residues that, when substituted with alanine, gave intermediate effects on affinity were extensively substituted to identify changes that improved affinity. Mutations that improved affinity may, when combined, achieve combinatorial increases in the affinity of IL-4 (or IL-4 related peptides) for IL-4Rα. Increases in affinity should correlate with increased potency.

Muteins were generated by site-directed mutagenesis, expressed in the baculovirus system, purified to homogeneity, quantitated by amino acid analysis, and evaluated in receptor binding assays. The amino acid sequence of mature human IL-4 (SEQ ID NO:1) used in this study is shown below; His at position 1 represents the N-terminus of the mature polypeptide. A-, C- and D-helices are indicated above their respective starting points, and underlined. Amino acids that, when appropriately substituted, yielded higher affinity variants, are shown in bold-faced type:

```
                A:→
His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr
                20                  25                  30
```

-continued

```
Asp Ile Phe Ala Ala Ser Lys Asn Thr Thr Glu Lys Glu Thr Phe
                35                  40                  45

Cys Arg Ala Ala Thr Val Leu Arg Gln Phe Tyr Ser His His Glu
                50                  55                  60

                                                C:→
Lys Asp Thr Arg Cys Leu Gly Ala Thr Ala Gln Gln Phe His Arg
                65                  70                  75

His Lys Gln Leu Ile Arg Phe Leu Lys Arg Leu Asp Arg Asn Leu
                80                  85                  90

Trp Gly Leu Ala Gly Leu Asn Ser Cys Pro Val Lys Glu Ala Asn
                95                  100                 105

                D:→
Gln Ser Thr Leu Glu Asn Phe Leu Glu Arg Leu Lys Thr Ile Met
                110                 115                 120

Arg Glu Lys Tyr Ser Lys Cys Ser Ser
                125
```

Mutations examined in this study were introduced into a known antagonist variant of human IL-4 containing two substitutions in the D-helix, R121D and Y124D (Tony H P, et al, Design of human interleukin-4 antagonists inhibiting interleukin-4-dependent and interleukin-13-dependent responses in T-cells and B-cells with high efficiency, *Eur. J. Biochem,* 225(2):659–65 (1994); this mutein is designated "IL-4[R121D/Y124D]"). Muteins were expressed in a baculovirus system, purified to homogeneity, and evaluated in a solid-phase IL-4Rα receptor binding assay. The biological significance of improved affinity for IL-4Rα was evaluated in T cell proliferation assays. As the IL-4[R121D/Y124D] mutein is an antagonist of IL-4, improved affinity for IL-4Rα should result in a decreased $IC_{50}$ for the higher affinity antagonist mutein ($IC_{50}$ is defined as the concentration of antagonist necessary to inhibit a defined agonist response 50%).

Example 1

Production of Muteins

Muteins were generated by site-directed mutagenesis using primers containing codons corresponding to the desired mutation essentially as described by Kunkel T A, Roberts J D, and Zakour R A, "Rapid and efficient site-specific mutagenesis without phenotypic selection", *Methods Enzymol* 154:367–382 (1987). Briefly, human IL-4 cDNA containing the restriction enzyme sites Bam HI and Xba I was subcloned into the M13 phage vector M13 mp19 (New England Biolabs, Beverly, Mass.) using the same sites. Wild-type IL-4 cDNA was obtained using Polymerase Chain Reaction ("PCR") from a cDNA pool generated from mRNA isolated from human peripheral blood lymphocytes induced 24 hours with phorbol 12-myristate 13-acetate (10 ng/ml). The PCR primers used were, for the 5' end of the IL-4 open reading frame,

5'-CGC GGA TCC ATG GGT CTC ACC TCC-3' (SEQ ID NO:2);

and for the 3' end of the IL-4 open reading frame,

5'-CGC TCT AGA CTA GCT CGA ACA CTT TGA AT-3' (SEQ ID NO:3).

Restriction enzyme sites BamHI (5'-end) and XbaI (3'-end) were incorporated into each oligonucleotide and are indicated by italics. The PCR conditions used were 1 minute at 94° C., 1 minute at 58.7° C., and 1 minute at 72° C. for 25 cycles. The correct IL-4 cDNA sequence so obtained was confirmed by sequencing using the Sequenase® sequencing kit (Amersham Life Sciences, Arlington Heights, Ill.) as described by the manufacturer. Uracil-containing single strand DNA (U-DNA) was obtained by transforming the *E. coli* strain CJ236 (Bio-Rad Laboratories, Hercules, Calif.) with IL-4 cDNA-containing M13 mp19. Site-directed mutagenesis utilized in general primers containing 15 nucleotides homologous to the template U-DNA 5' to the codon(s) targetted for mutagenesis, nucleotides that incorporate the desired change, and an additional 10 nucleotides homologous to the template U-DNA 3' of the last altered nucleotide. The D-helix mutations Arg-121 to Asp and Tyr-124 to Asp were introduced to the wild-type IL-4 sequence. Uracil DNA for this variant, termed IL-4[R121D/Y124D], was generated as described above. All mutations generated in these studies were generated using the IL-4[R121D/Y124D] template.

Primers were phosphorylated using T4 polynucleotide kinase (New England Biolabs, Beverly, Mass.) using the manufacturer's protocol. The phosphorylated primer was then annealed to the U-DNA template, and followed by extension with T7 DNA polymerase (Bio-Rad Laboratories, Hercules, Calif.) as described by the manufacturer (Bio-Rad Laboratories, Hercules, Calif.). Cells of the *E. coli* strain DH5a™ (GibcoBRL, Gaithersburg, Md.) were transformed with 5 μl of reaction mixture and plated in "LB medium" containing 0.7% agar. After incubation at 37° C., plaques were expanded by picking three individual plaques arising from each mutagenesis reaction and transferring to 2 mls of "LB media" and grown overnight at 37° C. Single strand DNA was isolated using an M13 purification kit (Qiagen, Inc., Chatsworth, Calif.) per manufacturer's protocol, and clones containing the desired mutation were identified by sequencing the single stranded DNA using the Sequenase® sequencing kit (Amersham Life Sciences, Arlington Heights, Ill.) per manufacturer's protocol. Replicative Form DNA (double stranded form of M13 phage) corresponding to plaques containing the correct mutated sequence of IL-4 was isolated using the Qiagen Plasmid Miniprep Kit (Qiagen, Inc., Chatsworth, Calif.). IL-4 mutein cDNA from was isolated using Bam HI and Xba I from the purified Replicative Form DNA, and subcloned to the plasmid vector pFastBac™1, (GibcoBRL, Gaithersburg, Md.). After subcloning, recombininant baculovirus DNA (hereafter referred to as Bacmid) was generated by transforming pFastBac™1 containing the mutein cDNA to the *E. coli* strain DH10Bac™ (GibcoBRL, Gaithersburg, Md.) as described by the manufacturer. Muteins were expressed in

*Spodoptera frugiperda* (*Sf*) 9 cells using the Bac-to-Bac‰ (GibcoBRL, Gaithersburg, Md.) baculovirus expression system. All insect cell incubations occurred at 28° C. Briefly, 2 ml cultures of *Sf* 9 cells were transfected with 5 μl of recombinant Bacmid using CellFECTIN™ (GibcoBRL, Gaithersburg, Md.). The supernatant was harvested 60 hours post-transfection, and used to infect a 100–200 ml culture of $1\times10^6$*Sf*9 cells/ml in Grace's media (GibcoBRL, Gaithersburg, Md.). Per manufacturer's protocol, the supernatants were harvested 48–60 hrs post-infection by centrifugation at 5000 rpm for 10 minutes in a Sorvall® RC-5B centrifuge using a GSA rotor (Dupont Instrument Co., Willmington, Del.) and assayed for virus titre (typically, $>1\times10^8$ plaque forming units/ml was obtained). For protein production, 2–$3\times10^6$ *Sf* 9 cells/ml in 500 mls of SF900 II media (GibcoBRL, Gaithersburg, Md.) were infected at a multiplicity of infection between 4–10 and the supernatant was harvested 60–72 hrs post-infection by centrifugation at 5000 rpm for 10 minutes in a Sorvall® RC-5B centrifuge using a GSA rotor (Dupont Instrument Co., Willmington, Del.) and filtered through a sterile 0.2 μM filter unit.

Example 2

Purification of Muteins

Anti-human IL-4 monoclonal antibodies C400.1 and C400.17 were generated using standard protocols from mice using recombinant human IL-4 (Genzyme Diagnostics, Cambridge, Mass.) as immunogen, were produced as ascites fluid, purified, and coupled to CNBr-activated Sepharose (Pharmacia, Uppsala, Sweden) as per manufacturer's protocol. *Sf* 9 cell supernatants generated from infection of *Sf* 9 cells by recombinant baculovirus containing the respective IL-4 mutein were loaded onto a 1 ml column of anti-IL-4 MAb-coupled Sepharose, washed with 100 mM $NaHCO_3$, 500 mM NaCl, pH 8.3, washed with water to remove salt, and eluted with 8 column volumes of 100 mM Glycine, pH 3.0. Fractions were collected in siliconized vials containing 0.1 volume 1M Tris, pH 8.0. Mutein protein was further purified by reverse phase chromatography using a Dynamax®-300Å$C_{18}$ column (Rainin Instrument Co., Woburn, Mass.) with a 0–100% gradient of Buffer A to B (Buffer A, water; Buffer B, acetonitrile, 0.1% trifluoroacetic acid). Fractions were evaluated by SDS-PAGE, and mutein-containing fractions were lyophilized for storage, and resuspended in sterile phosphate-buffered saline (PBS; 10 mM $NaPO_4$, 137 mM NaCl, pH 7.6) for assays. Mutein so purified was typically a single band as observed by SDS-PAGE (silver stain), and was quantitated by amino acid analysis (accuracy typically >90%).

Example 3

Receptor Binding Assays

Figure 2:
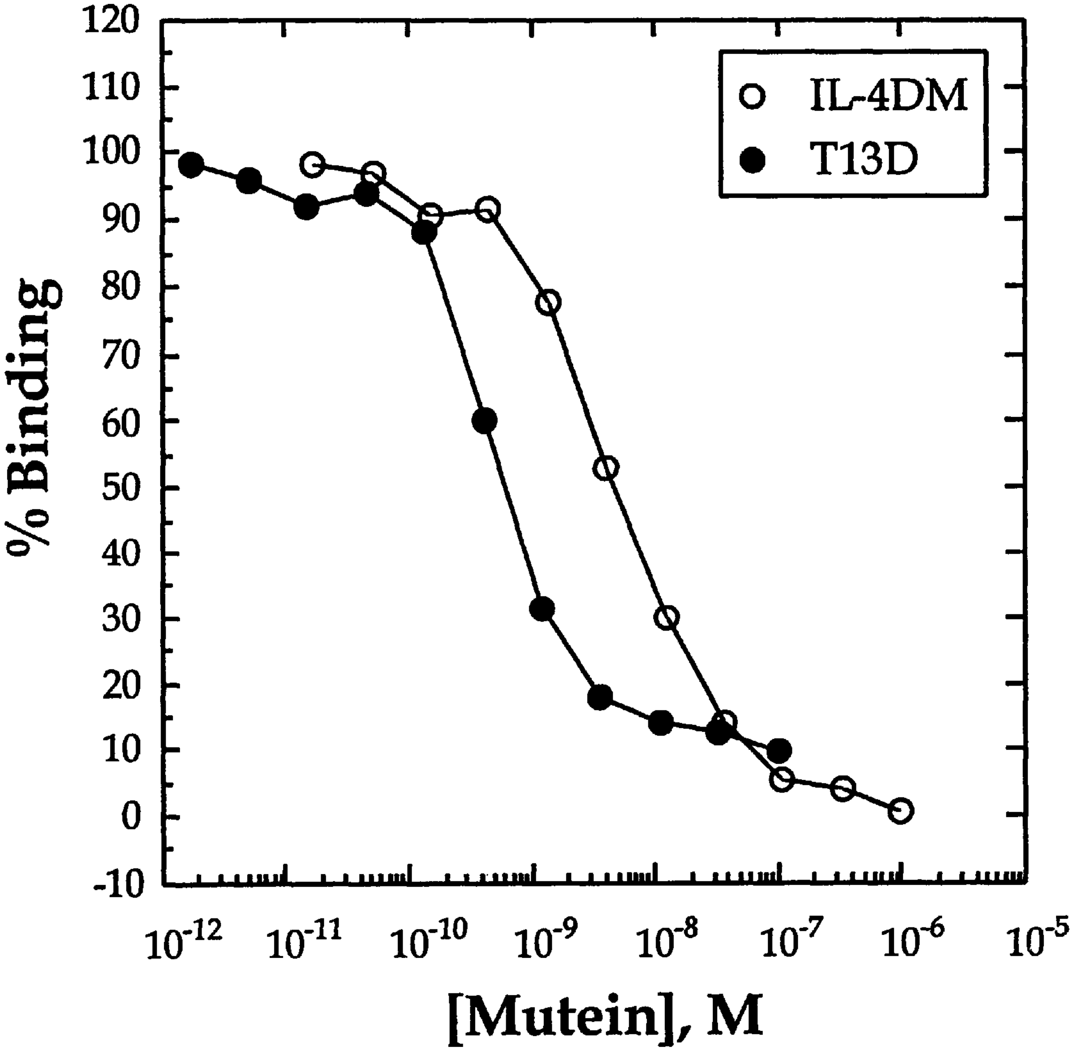
FIG. 2 is an X-Y plot of the competitive binding of T13D-IL-4[R121D/Y124D]. The ability of T13D-IL-4 [R121D/Y124D], •, to compete $^{125}$I-IL-4 in a solid phase binding assay is shown relative to that of IL-4[R121D/Y124D], ○. The $K_d$ determined using this assay for T13D-IL-4[R121D/Y124D] was 0.28 nM, and for IL-4[R121D/Y124D] 5.0 nM.

In order to determine the effects of substitution on the ability of IL-4 muteins to bind to IL-4Rα (Ldzerda, R. L., et. al., Human interleukin 4 receptor confers biological responsiveness and defines a novel receptor superfamily, *J. Exp. Med.* 171:861–873(1990)), a solid-phase receptor binding assay was developed. Briefly, the affinity of muteins was measured by their ability to displace radiolabelled IL-4 from IL-4Rα bound to a solid surface. FIG. 2 shows the ability of T13D-IL-4[R121D/Y124D] to compete $^{125}$I-IL-4 in a solid phase binding assay relative to that of IL-4[R121D/Y124D]. The assay was formatted using 96-well FlashPlates® (DuPont NEN®, Boston, Mass.) coated with streptavidin; the extracellular domain of IL-4Rα was bound to these plates by virtue of a peptide tag engineered to the extracellular domain of IL-4Rα that binds streptavidin. FlashPlates contain a scintillant impregnated into the plastic of the plate, which has the property that only radiolabelled compound in close proximity to the surface of the plate will incite scintillation. Samples containing radiolabelled IL-4 and IL-4 antagonist mutein were added to each well, and incubated until equilibrium was obtained. Because non-bound radiolabelled compound does not induce a scintillation signal, no washing step was required before assessing the amount of radioactivity bound in each well. The radioactivity measured thus represents the amount of radiolabelled IL-4 bound to IL-4Rα, and, upon consideration of the quantity of unlabelled IL-4 antagonist mutein added, allows the calculation of the affinity of the unlabelled IL-4 antagonist mutein for IL-4Rα. An internal standard was generated in each assay by measuring the affinity of IL-4[R121D/Y124D] in parallel with each mutein. Thus, specific relative measures of affinity could be obtained, which allowed the assessment of the effect of individual substitutions on the affinity for IL-4Rα.

The extracellular domain of IL-4Rα was recovered using PCR from a Jurkat cell lgt11 library (Stratagene Cloning Systems, La Jolla, Calif.). The PCR primers used to isolate the extracellular domain of IL-4Rα were, for the 5' end of the IL-4Rα open reading frame,

5' GGC ATG GAT CCA TGG GGT GGC TTT GCT CTG G 3' (SEQ ID NO:4);

and for the 3' end of the extracellular domain of IL-4Rα,

5' AAG CCG CTA GCG CTG TGC TGC TCG AAG GGC 3' (SEQ ID NO:5).

The PCR conditions used were 1 minute at 94° C., 1 minute at 65.8° C., and 1 minute at 72° C. for 30 cycles. The resultant PCR product was digested with the restriction enzymes BamHI and Eco47III, and subcloned into a pBluescript® vector (Stratagene Cloning Systems, La Jolla, Calif.) containing DNA with the codons corresponding to the sequence Ser-Ala-Trp-Arg-His-Pro-Gln-Phe-Gly-Gly (SEQ ID NO: 6) digested with the same enzymes. This sequence has been reported to bind to streptavidin (Schmidt T G and Skerra, A., The random peptide library-assisted engineering of a C-terminal affinity peptide, useful for the detection and purification of a functional Ig Fv fragment, *Protein Eng,* 6(1):109–122 (1992)). The extracellular domain of IL-4Rα so generated encoded the peptide sequence Ser-Ala-Trp-Arg-His-Pro-Gln-Phe-Gly-Gly (SEQ ID NO: 6) at the C-terminus of the extracellular domain, and was termed sIL-4Rα-STX (Met at position 1 is the N-terminus of the mature IL-4Rα) and is SEQ ID NO: 7.

sIL-4Rα-STX protein was produced using the baculovirus system in a manner identical to that used for IL-4 antagonist muteins, purified by affinity chromatography with an IL-4-coupled matrix as described (Kruse N, et. al., "Two distinct functional sites of human interleukin 4 are identified by variants impaired in either receptor binding or receptor activation." *EMBO J.,* 12(13) p5121–9(1993).), and stored in PBS. The IL-4 matrix was generated by coupling IL-4 produced in *E. coli* to CNBr Sepharose 4B as described by the manufacturer (Pharmacia, Uppsala, Sweden). Streptavidin-coated FlashPlates® (DuPont NEN®, Boston, Mass.) were coated with 100 μl of 2 μg/ml sIL-4Rα-STX in 100 mM Tris, 0.1% BSA, pH 7.0 for 2 hrs at 20° C., washed with PBS, 0.1% BSA, pH 7.6, and incubated with 200 pM $^{125}$I-IL-4 (DuPont NEN®, Boston, Mass.) and varying concentrations of IL-4 antagonist mutein in 100 μl PBS, 0.1% BSA, pH 7.6 for 1.5 hours at 20° C. in quadruplicate. Assays were repeated at least twice. As an internal reference, IL-4[R121D/Y124D] was titrated in parallel with each mutein on the same Flashplate®. Bound radioactivity was measured in a TopCount' scintillation counter (Packard Instrument Co., Meriden, Conn.), and $K_d$ values were calculated using the Ligand program (Munson, P. J. and Rodbard, D., "Computerized Analysis of Ligand Binding Data". *Meth. Enzymol.,* 92 p543–576 (1983)); error in the Kd values, expressed as % CV, was between 2–20%. Results were expressed as the ratio of $K_d$ mutein/$K_d$ IL-4[R121D/Y124D] using data acquired from within each assay plate. Differences between Kd values measured reflect either a relative increase in affinity of the respective mutein for IL-4Rα (i.e., $K_d$ mutein/$K_d$ IL-4[R121D/Y124D]<1), or a relative decrease in affinity of the respective mutein for IL-4Rα (i.e., $K_d$ mutein/$K_d$ IL-4[R121D/Y124D]>1).

Example 4

1° T Cell Proliferation Assay

Primary T cells were obtained from fresh blood from normal donors and purified by centrifugation using Ficoll-Paque® Plus (Pharmacia, Upsalla, Sweden) essentially as described by Kruse, N., Tony, H. P. and Sebald, W., Conversion of human interleukin-4 into a high affinity antagonist by a single amino acid replacement, *Embo J.* 11:3237–44 (1992). The purified peripheral blood mononuclear cells were incubated for 7 days with 10 μg/ml phytohemagglutinin (Sigma Chemical Co., St. Louis, Mo.), harvested by centrifugation, and washed in RPMI 1640 media (GibcoBRL, Gaithersburg, Md.). $5\times10^4$ activated T cells/well (PHA-blasts) were incubated with varying amounts of IL-4 or mutein in RPMI 1640 media containing 10% fetal bovine serum, 10 mM HEPES, pH 7.5,2 mM L-glutamine, 100 units/ml penicillin G, and 100 μg/ml streptomycin sulphate in 96 well plates for 48 hrs at 37° C., pulsed with 1 μCi $^3$H-thymidine (DuPont NEN®, Boston, Mass.)/well for 6 hrs, harvested, and radioactivity was measured in a TopCount' scintillation counter (Packard Instrument Co., Meriden, Conn.).

Example 5

Effect of Alanine Substitution on the Affinity of IL-4 for IL-4Rα

The effects of alanine substitution of the surface-exposed residues of helices A- and C- of IL-4 on the affinity of IL-4 for IL-4Rα are shown in Table I.

TABLE I

Results of the alanine-scan of the surface-exposed residues of the A- and C-helices of IL-4*

| Mutation | $K_d$ mutein/$K_d$ IL-4[R121D/Y124D] |
|---|---|
| A-helix: | |
| Ile-5 to Ala | 71 |
| Gln-8 to Ala | 1.1 |
| Glu-9 to Ala | 125 |
| Ile-11 to Ala | 3.3 |
| Lys-12 to Ala | 1.0 |
| Thr-13 to Ala | 6.4 |
| Asn-15 to Ala | 1.8 |
| Ser-16 to Ala | 0.43 |
| C-helix: | |
| His-74 to Ala | 1.9 |
| Lys-77 to Ala | 3.7 |
| Gln-78 to Ala | 4.7 |
| Arg-81 to Ala | 8.9 |
| Phe-82 to Ala | 2.3 |
| Lys-84 to Ala | 11 |
| Arg-85 to Ala | 4.2 |
| Arg-88 to Ala | 150 |
| Asn-89 to Ala | 51 |
| Trp-91 to Ala | 2.3 |

*All mutations were superimposed upon the IL-4[R121D/Y124D] backbone.

As alanine substitution generally does not cause structural changes in the protein fold, effects on activity, in this case affinity, can be ascribed to the loss of the side chain substituted (Cunningham, B. C., Wells, J. A., High-resolution epitope mapping of hGH-receptor interactions by alanine-scanning mutagenesis, *Science* 244(4908):1081–5 (1989). Nominal changes in affinity (e.g., ~2-fold) that result as a consequence of alanine substitution suggest that the residue/position substituted is not involved in the interaction; large effects (e.g., >100-fold) suggest that the residue/position substituted is critical for the interaction (Lowman H B, et. al., "Selecting high-affinity binding proteins by monovalent phage display". *Biochemistry* 30(45) p10832–8 (1991)). Lowman, et. al., (ibid.) found that those residues displaying intermediate effects in binding as a consequence of alanine substitution were, in addition to the most sensitive residues, involved with the interaction being studied.

Applying these conclusions to the results of this alanine scan of the A- and C-helices of IL-4, the most critical residues for the interaction of IL-4 with IL-4Rα are Glu-9 and Arg-88; intermediate residues would include Ile-5>Asn89>Lys-84~Arg-81>Thr-13~Gln-78~Arg-85~Lys-77; residues likely not involved in the interaction include Gln-8, Ile-11, Lys-12, Asn-15, His-74, Phe-82, and Trp-91. Ser-16, by virtue of the observed increase in affinity when substituted with alanine, is at or within the interface formed between IL-4 and IL-4Rα. These results define a probable binding surface of IL-4 for IL-4Rα, that when put in context of the structure of IL-4 (Smith L J, et. al., Human interleukin 4. The solution structure of a four-helix bundle protein, *J. Mol. Biol.* 224(4):899–904 (1992)), consists of adjacent portions of the A- and C-helices of IL-4, and extends for about three helical turns on each helix, i.e., positions 5–16 on the A helix, and 77–89 on the C helix. The most likely residues involved in the contact with the IL-4 receptor alpha are, in the A-helix: Ile-5, Glu-9, Thr-13, and Ser-16; in the C-helix: Lys-77, Gln-78, Arg-81, Lys-84, Arg-85, Arg-88, and Asn-89. Structurally, the critical center of interaction appears to be composed of residues Glu-9, Arg-88, and Asn-89, and the observed alanine effect generally decreases as one moves away from this portion of the molecule. This analysis thus describes a binding surface of IL-4 for IL-4Rα.

Example 6

Substitution Muteins at Selected Positions

In a previous analysis of growth hormone, substitutions for residues that, when substituted with alanine had an intermediate effect on affinity, were found that improved the affinity of growth hormone for its receptor (Lowman H B, et. al., "Selecting high-affinity binding proteins by monovalent phage display". *Biochemistry* 30(45) p10832–8(1991)). It was found that the nature of the substitution of a given residue that resulted in improved affinity was not predictable. Thus, in the analysis presented here, all substitutions that would have no inherent structural effects (i.e., exclusive of Cys, Gly, Pro) or undergo facile oxidative reactions (i.e., exclusive of Met) were introduced at the targetted positions:

TABLE II

Targetted residues and their substitutions*

| Residue | Ala-effect | Substitutions |
|---|---|---|
| Ile-5 | 71 | D, E, F, H, K, L, N, Q, R, S, T, V, W, Y |
| Thr-13 | 6.4 | D, E, F, H, I, K, L, N, Q, R, S, V, W, Y |
| Ser-16 | 0.43 | D, E, F, H, I, K, L, N, Q, R, T, V, W, Y |
| Arg-81 | 8.9 | D, E, F, H, I, K, L, N, Q, S, T, V, W, Y |
| Asn-89 | 51 | D, E, F, H, I, K, L, Q, R, S, T, V, W, Y |

*All mutations were superimposed upon the IL-4[R121D/Y124D] backbone.

Cysteine, glycine, methionine, and proline were thus excluded from this further substitution analysis. Residues were chosen for further analysis if, upon alanine substitution, there was a decrease in affinity between 5 and 80-fold or any increase in affinity; this range was chosen based on the results obtained by Lowman, et.al. (ibid). Additionally, Ser-16 was selected for further analysis because of the observed increase in affinity that resulted from alanine substitution; this suggested that other substitutions at this position may also yield affinity improvements.

Example 7

Substitutions that Yielded Improved Affinity for IL-4Rα

Muteins containing substitutions at individual positions in the A- and C-helices were generated in combination with IL-4[R121D/Y124D] backbone; competitive binding assays were performed such that each mutein was compared in parallel with IL-4[R121D/Y124D]. This allowed direct comparisons and thus conclusions about the effect of each substitution on the affinity of the specific mutein for IL-4Rα.

All substitutions that resulted in improved affinity are shown in Table III. The ratio "$K_d$ IL-4[R121D/Y124D]/$K_d$ mutein" indicates the relative increase in affinity observed as a consequence of each substitution.

TABLE III

| Substitution | $K_d$ IL-4[R121D/Y124D]/$K_d$ mutein |
|---|---|
| T13D-IL-4[R121D/Y124D] | 18 |
| S16A-IL-4[R121D/Y124D] | 2.5 |
| S16D-IL-4[R121D/Y124D] | 3.1 |
| S16H-IL-4[R121D/Y124D] | 1.5 |
| S16I-IL-4[R121D/Y124D] | 1.8 |
| S16L-IL-4[R121D/Y124D] | 2.9 |
| S16Q-IL-4[R121D/Y124D] | 2.3 |
| S16R-IL-4[R121D/Y124D] | 1.8 |
| S16T-IL-4[R121D/Y124D] | 2.4 |
| S16V-IL-4[R121D/Y124D] | 2.0 |
| S16Y-IL-4[R121D/Y124D] | 1.8 |
| R81K-IL-4[R121D/Y124D] | 1.8 |
| N89I-IL-4[R121D/Y124D] | 2.0 |

Most substitutions were either deleterious or had no effect on the affinity for IL-4Rα (data not shown). However, several substitutions did improve the affinity, the most notable of which was the Thr-13 to Asp substitution that resulted in a surprising 18-fold affinity increase for IL-4Rα (FIG. 2). The amino acid Ser-16 was unique in this analysis wherein most substitutions resulted in modest increases in affinity. Similar competitive binding profiles were obtained for these other muteins in correlation with their relative affinity (data not shown).

Affinity improvements are relative to the IL-4[R121D/Y124D] parent protein. It is anticipated that combining these substitutions in one protein may result in combinatorial increases in affinity; e.g., [T13D/N89I]-IL-4[R121D/Y124D] may produce a mutein with 36-fold greater affinity than IL-4[R121D/Y124D].

Residues Thr-13 and Ser-16 yielded the best improvements in affinity when the appropriate substitution was identified. This would suggest that other residues that, when substituted with alanine gave similar effects as either mutein T13A or S16A (6.4-fold decrease and 2.5-fold increase, repectively), would also likely yield higher affinity IL-4 variants when appropriately substituted. For the current series of alanine-substituted residues, this would include: Ile-11, Lys-77, Gln-78, Lys-84 and Arg-85.

For growth hormone, which has been extensively studied, single substitutions which resulted in increases in affinity were on the order of 1.5- to 5-fold (Lowman H B; Wells J A, "Affinity maturation of human growth hormone by monovalent phage display". *J. Mol. Biol.* 234(3) p564–78 (1993)). Recently, however, substitutions that have resulted in large improvements in either activity (human IL-3 (Olins PO, et.al., Saturation mutagenesis of human interleukin-3, *J. Biol. Chem.* 270(40):23754–60(1995)) or affinity (human ciliary neurotrophic factor (CNTF) (Saggio I, et. al., CNTF variants with increased biological potency and receptor selectivity define a functional site of receptor interaction, *EMBO J.* 14(13):3045–54 (1995))) have been identified. For IL-3 one mutation increased in vitro biological activity ~26-fold; for CNTF, a single substitution increased affinity ~32-fold. For other cytokines in the literature, most substitutions generally resulted in no effect or losses of affinity/activity. Thus, the absolute effect of any given substitution on affinity and/or activity is unpredictable.

Example 8

Effect of T13D Substitution on Biological Activity

The IL-4 antagonist mutein IL-4[R121D/Y124D] is an antagonist of IL-4 (Tony H P, Shen B J, Reusch P, and Sebald W, "Design of human interleukin-4 antagonists inhibiting interleukin-4-dependent and interleukin-13-dependent responses in T-cells and B-cells with high efficiency.". *Eur. J. Biochem.*, 225(2) p659–65 (1994)), and was used as the 'baseline' peptide in this study due to its inability to stimulate IL-4 activities. This antagonist mutein is thought to be an antagonist by virtue of its ability to bind IL-4Rα but not engage $g_c$ in a signaling competent manner, thus blocking IL-4 from binding to its cognate receptor complex. Thus, the biological effects of IL-4[R121D/Y124D] (IL-4 antagonism) are isolated to its interactions, measured by affinity, with IL-4Rα.

Figure 3:
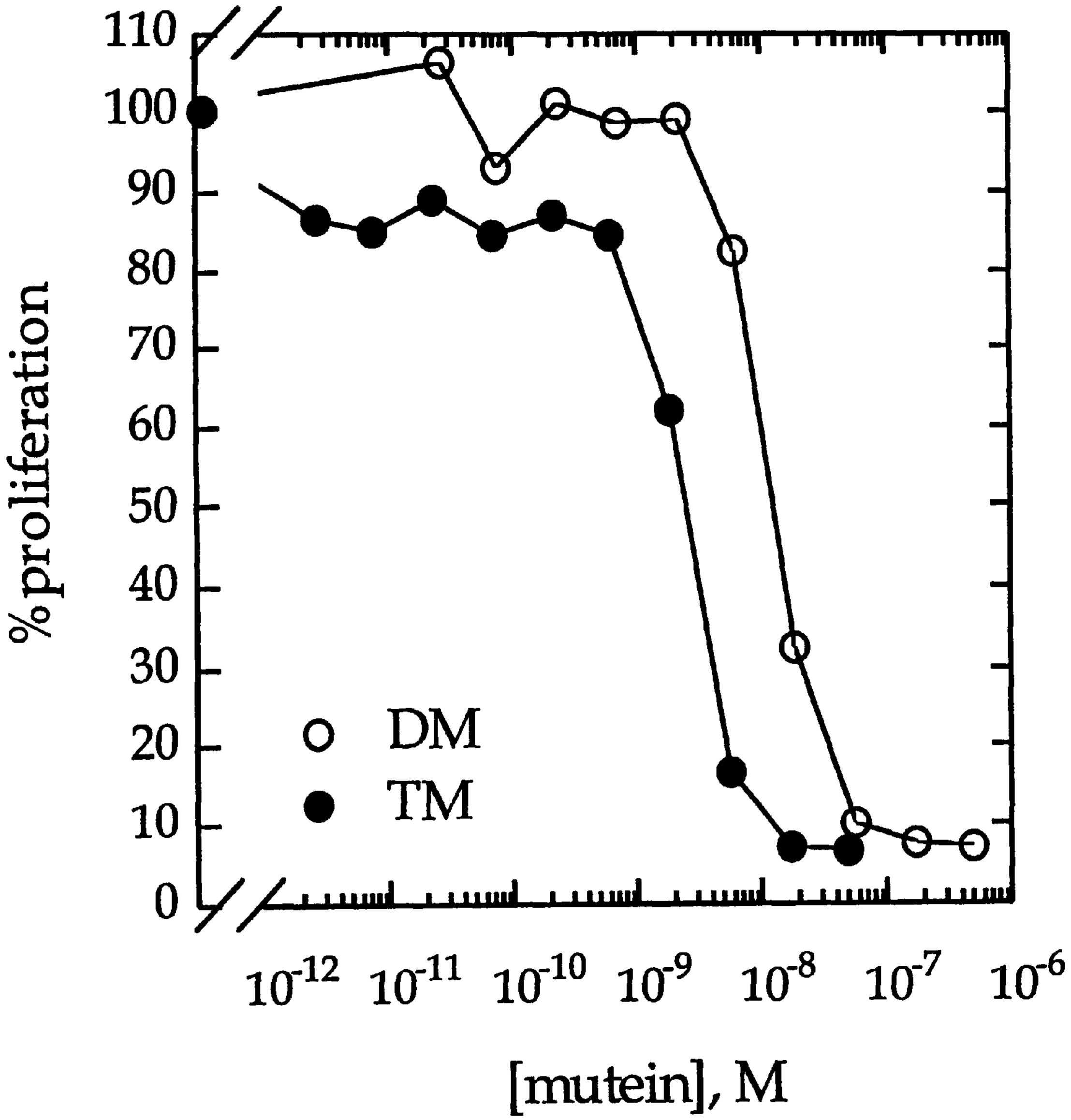
FIG. 3 is a similar X-Y plot depicting antagonism of IL-4 by T13D-IL-4[R121D/Y124D], ○. The ability of T13D-IL-4[R121D/Y124D] to compete IL-4-induced proliferation of PHA-blasts is shown relative to IL-4[R121D/Y124D], •. The $IC_{50}$ determined from this assay for T13D-IL-4[R121D/Y124D] was 2 nM, and for IL-4[R121D/Y124D], 13 nM.

In order to prove that receptor affinity correlates with biological potency, the mutein T13D-IL-4[R121D/Y124D] was evaluated for its ability to inhibit IL-4-induced proliferation of PHA-blasts (FIG. 3). The observed $IC_{50}$ (concentration at which 50% inihibition is seen) relative to IL-4[R121D/Y124D] was found to be approximately proportional to the observed relative change in receptor affinity.

In conclusion, although binding with higher affinity to IL-4Rα, T13D-IL-4[R121D/Y124D] remains an IL-4 antagonist. The $IC_{50}$ for T13D-IL-4[R121D/Y124D] vs. the IL-4[R121D/Y124D] is approximately proportional to the relative $K_d$ values (as measured in the solid phase binding assay) obtained for these two proteins: the $K_d$ of T13D-IL-4[R121D/Y124D] is ~18-fold lower than the $K_d$ of IL-4 [R121D/Y124D] (0.28 nM vs. 5.0 nM, respectively); the $IC_{50}$ of T13D-IL-4[R121D/Y124D] is ~5–10-fold lower than the $IC_{50}$ of IL-4[R121D/Y124D] (2 nM vs. 13 nM, respectively). The specific numerical differences in relative effect may be a consequence of the particular conditions of each assay: 1.5 hrs incubation for the solid-phase binding assay at 20° C. vs. 48 hrs incubation at 37° C. for the proliferation assay. The ability of other muteins evaluated in this study to compete IL-4 in biological assays was also proportional to their relative Kd to the IL-4[R121D/Y124D] (data not shown). These results indicate that binding to IL-4Rα is a separable event from activation of the IL-4 receptor; this activation requires the heterodimerization of IL-4Rα and at least one other subunit (e.g., gc). Thus, modification to IL-4 in the A- and C-helix modulates the affinity of IL-4 for IL-4Rα, and does so in a proportionate manner to the ability of said mutein to antagonize IL-4 in a biological context. This affinity effect, by virtue of the mechanism of interaction of IL-4 with its receptor, should also translate to increasing the potency of IL-4-derived agonist peptides.

The theories of this invention may also be adapted to other cytokines. The most obvious target is IL-13 due to the fact that the IL-13 receptor complex also utilizes IL-4Rα (Zurawski S. M., et al., The primary binding subunit of the human interleukin-4 receptor is also a component of the interleukin-13 receptor, *J. Biol. Chem.* 270:13869–78 (1995). Therefore, mutating the A- and C-helices of IL-13 to more closely resemble those of IL-4 should result in an increase in binding affinity for IL-4Rα.

An alignment of the two interleukins enables identification of the positions that would be analogous to a target mutation site, for example, Thr 13 on IL-4. The binding surfaces of the two interleukins are compared in Table IV below.

TABLE IV

Comparison of the A- and C-helices of IL-4 with the Sequences of IL-13*

| | Residue positions | Sequence |
|---|---|---|
| A-helix: | | |
| hIL-4 | 5–17 | . . . ITLQEIIKTLNSL . . . |
| hIL-13 | 4–16 | . . . TALRELIEELVNI . . . |
| C-helix: | | |
| hIL-4 | 74–91 | . . . HKQLIRFLKRLDRNLW . . . |
| hIL-13 | 59–74 | . . . TQRMLSGFCPHKVSAG . . . |

*Alignment from: Bamborough, P., Duncan, D., and Richards, W. G., "Predictive Modelling of the 3-D Structure of Interleukin-13", Protein Engineering, 7, pp. 1007–82 (1994)

The most critical residues of IL-4 mediating the interactions with IL-4Rα identified from the alanine-scan, Glu-9 and Arg-88, are shown in bold-faced type, as are the corresponding residues in IL-13 based on this sequence alignment. As previously mentioned, IL-13 utilizes the IL-4Rα chain in its receptor complex (Zurawski S. M., et al., supra). Thus, changing the A- and C-helices of IL-13 to more closely resemble those of IL-4 should result in an increase in binding affinity for IL-4Rα. Additionally, substitution of positionally-equivalent IL-13 residues with residues found to increase the affinity of IL-4 for IL-4Rα (positions shown double-underlined for IL-4 and IL-13) should also result in increased affinity of IL-13 for its receptor complex, and thus improved potency.

Sequences

The following biological sequences are contained herein:

SEQ ID NO: 1: amino acid sequence, mature human IL-4;

SEQ ID NO: 2: nucleotide sequence, PCR primers;

SEQ ID NO: 3: nucleotide sequence, PCR primers;

SEQ ID NO: 4: nucleotide sequence, PCR primers;

SEQ ID NO: 5: nucleotide sequence, PCR primers;

SEQ ID NO: 6: amino acid sequence of peptide tag for streptavidin;

SEQ ID NO: 7: amino acid sequence of sIL-4Rα-STX;

SEQ ID NO: 8: amino acid, nucleotide sequence of T13D-1L4; and

SEQ ID NO: 9: amino acid, nucleotide sequence of T13D-IL4[R121D/Y124D].

Other embodiments of the invention will become apparent to one of skill in the art. The concept and experimental approach described herein should be applicable to other cytokines utilizing heterologous multimeric receptor systems, in particular IL-2 and related cytokines (e.g., IL-7, IL-9, IL-10, IL-13 and IL-15), interferon alpha, and interferon gamma.

SEQUENCE LISTING

```
(1) GENERAL INFORMATION:

   (iii) NUMBER OF SEQUENCES: 9


(2) INFORMATION FOR SEQ ID NO: 1:

     (i) SEQUENCE CHARACTERISTICS:
          (A) LENGTH: 129
          (B) TYPE: amino acid
          (C) STRANDEDNESS: single
          (D) TOPOLOGY: linear

    (ii) MOLECULE TYPE: protein
          (A) DESCRIPTION: human Interleukin-4 protein

   (iii) HYPOTHETICAL: no

    (iv) ANTI-SENSE: no
```

-continued (xi) SEQUENCE DESCRIPTION: SEQ ID NO: 1:

```
His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr
                20                  25                  30

Asp Ile Phe Ala Ala Ser Lys Asn Thr Thr Glu Lys Glu Thr Phe
                35                  40                  45

Cys Arg Ala Ala Thr Val Leu Arg Gln Phe Tyr Ser His His Glu
                50                  55                  60

Lys Asp Thr Arg Cys Leu Gly Ala Thr Ala Gln Gln Phe His Arg
                65                  70                  75

His Lys Gln Leu Ile Arg Phe Leu Lys Arg Leu Asp Arg Asn Leu
                80                  85                  90

Trp Gly Leu Ala Gly Leu Asn Ser Cys Pro Val Lys Glu Ala Asn
                95                  100                 105

Gln Ser Thr Leu Glu Asn Phe Leu Glu Arg Leu Lys Thr Ile Met
                110                 115                 120

Arg Glu Lys Tyr Ser Lys Cys Ser Ser
                125
```

(2) INFORMATION FOR SEQ ID NO: 2:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: cDNA
(A) DESCRIPTION: 5' PCR Primer, IL-4

(iii) HYPOTHETICAL: no (iv) ANTI-SENSE: no (xi) SEQUENCE DESCRIPTION: SEQ ID NO: 2:

CGCGGATCCA TGGGTCTCAC CTCC 24

(2) INFORMATION FOR SEQ ID NO: 3:

(i) SEQUENCE CHARACTERISTICS:
(A) LENGTH: 29
(B) TYPE: nucleic acid
(C) STRANDEDNESS: single
(D) TOPOLOGY: linear (ii) MOLECULE TYPE: cDNA
(A) DESCRIPTION: 3' PCR Primer, IL-4

(iii) HYPOTHETICAL: no (iv) ANTI-SENSE: no (xi) SEQUENCE DESCRIPTION: SEQ ID NO: 3:

CGCTCTAGAC TAGCTCGAAC ACTTTGAAT 29

(2) INFORMATION FOR SEQ ID NO: 4:

(i) SEQUENCE CHARACTERISTICS:
(A) LENGTH: 31
(B) TYPE: nucleic acid
(C) STRANDEDNESS: single
(D) TOPOLOGY: linear -continued (ii) MOLECULE TYPE: cDNA
(A) DESCRIPTION: 5' PCR Primer, IL-4R( (ED)

(iii) HYPOTHETICAL: no (iv) ANTI-SENSE: no (xi) SEQUENCE DESCRIPTION: SEQ ID NO: 4:

GGCATGGATC CATGGGGTGG CTTTGCTCTG G 31

(2) INFORMATION FOR SEQ ID NO: 5:

(i) SEQUENCE CHARACTERISTICS:
(A) LENGTH: 30
(B) TYPE: nucleic acid
(C) STRANDEDNESS: single
(D) TOPOLOGY: linear (ii) MOLECULE TYPE: cDNA
(A) DESCRIPTION: 3' PCR Primer, IL-4R( (ED)

(iii) HYPOTHETICAL: no (iv) ANTI-SENSE: no (xi) SEQUENCE DESCRIPTION: SEQ ID NO: 5:

AAGCCGCTAG CGCTGTGCTG CTCGAAGGGC 30

(2) INFORMATION FOR SEQ ID NO: 6:

(i) SEQUENCE CHARACTERISTICS:
(A) LENGTH: 10
(B) TYPE: amino acid
(C) STRANDEDNESS: single
(D) TOPOLOGY: linear (ii) MOLECULE TYPE: peptide
(A) DESCRIPTION: tag for streptavidin (iii) HYPOTHETICAL: no (iv) ANTI-SENSE: no (xi) SEQUENCE DESCRIPTION: SEQ ID NO: 6:

```
Ser Ala Trp Arg His Pro Gln Phe Gly Gly                         10
1               5                   10
```

(2) INFORMATION FOR SEQ ID NO: 7:

(i) SEQUENCE CHARACTERISTICS:
(A) LENGTH: 197
(B) TYPE: amino acid
(C) STRANDEDNESS: single
(D) TOPOLOGY: linear (ii) MOLECULE TYPE: protein
(A) DESCRIPTION: sIL-4R(-STX (iii) HYPOTHETICAL: no (iv) ANTI-SENSE: no (xi) SEQUENCE DESCRIPTION: SEQ ID NO: 7:

```
Met Lys Val Leu Gln Glu Pro Thr Cys Val Ser Asp Tyr Met Ser
1               5                   10                  15

Ile Ser Thr Cys Glu Trp Lys Met Asn Gly Pro Thr Asn Cys Ser
                20                  25                  30

Thr Glu Leu Arg Leu Gly Ala Gly Cys Val Cys His Leu Leu Met
                35                  40                  45
```

-continued

```
Asp Asp Val Val Ser Ala Asp Asn Tyr Thr Leu Asp Leu Trp Ala
                50                  55                  60

Gly Gln Gln Leu Leu Trp Lys Gly Ser Phe Lys Pro Ser Glu His
                65                  70                  75

Val Lys Pro Arg Ala Pro Gly Asn Leu Thr Val His Thr Asn Val
                80                  85                  90

Ser Asp Thr Leu Leu Leu Thr Trp Ser Asn Pro Tyr Pro Pro Asp
                95                  100                 105

Asn Tyr Leu Tyr Asn His Leu Thr Tyr Ala Val Asn Ile Trp Ser
                110                 115                 120

Glu Asn Asp Pro Ala Asp Phe Arg Ile Tyr Asn Val Thr Tyr Leu
                125                 130                 135

Glu Pro Ser Leu Arg Ile Ala Ala Ser Thr Leu Lys Ser Gly Ile
                140                 145                 150

Ser Tyr Arg Ala Arg Val Arg Ala Trp Ala Gln Cys Tyr Asn Thr
                155                 160                 165

Thr Trp Ser Glu Trp Ser Pro Ser Thr Lys Trp His Asn Ser Tyr
                170                 175                 180

Arg Glu Pro Phe Glu Gln His Ser Ala Trp Arg His Pro Gln Phe
                185                 190                 195

Gly Gly
```

(2) INFORMATION FOR SEQ ID NO: 8:

(i) SEQUENCE CHARACTERISTICS:
(A) LENGTH: 462
(B) TYPE: nucleic acid
(C) STRANDEDNESS: single
(D) TOPOLOGY: linear (ii) MOLECULE TYPE: cDNA
(A) DESCRIPTION: IL-4/T13D (iii) HYPOTHETICAL: no (iv) ANTI-SENSE: no (xi) SEQUENCE DESCRIPTION: SEQ ID NO: 8:

```
ATG GGT CTC ACC TCC CAA CTG CTT CCC CCT CTG TTC TTC CTG CTA            45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC            90
Ala Cys Ala Gly Asn Phe Val His Gly His Lys Cys Asp Ile Thr
                20                  25                  30

TTA CAG GAG ATC ATC AAA GAT TTG AAC AGC CTC ACA GAG CAG AAG           135
Leu Gln Glu Ile Ile Lys Asp Leu Asn Ser Leu Thr Glu Gln Lys
                35                  40                  45

ACT CTG TGC ACC GAG TTG ACC GTA ACA GAC ATC TTT GCT GCC TCC           180
Thr Leu Cys Thr Glu Leu Thr Val Thr Asp Ile Phe Ala Ala Ser
                50                  55                  60

AAG AAC ACA ACT GAG AAG GAA ACC TTC TGC AGG GCT GCG ACT GTG           225
Lys Asn Thr Thr Glu Lys Glu Thr Phe Cys Arg Ala Ala Thr Val
                65                  70                  75

CTC CGG CAG TTC TAC AGC CAC CAT GAG AAG GAC ACT CGC TGC CTG           270
Leu Arg Gln Phe Tyr Ser His His Glu Lys Asp Thr Arg Cys Leu
                80                  85                  90

GGT GCG ACT GCA CAG CAG TTC CAC AGG CAC AAG CAG CTG ATC CGA           315
Gly Ala Thr Ala Gln Gln Phe His Arg His Lys Gln Leu Ile Arg
                95                  100                 105

TTC CTG AAA CGG CTC GAC AGG AAC CTC TGG GGC CTG GCG GGC TTG           360
```

-continued

```
Phe Leu Lys Arg Leu Asp Arg Asn Leu Trp Gly Leu Ala Gly Leu
                110                 115                 120

AAT TCC TGT CCT GTG AAG GAA GCC AAC CAG AGT ACG TTG GAA AAC          405
Asn Ser Cys Pro Val Lys Glu Ala Asn Gln Ser Thr Leu Glu Asn
                125                 130                 135

TTC TTG GAA AGG CTA AAG ACG ATC ATG AGA GAG AAA TAT TCA AAG          450
Phe Leu Glu Arg Leu Lys Thr Ile Met Arg Glu Lys Tyr Ser Lys
                140                 145                 150

TGT TCG AGC TAG                                                      462
Cys Ser Ser End
```

(2) INFORMATION FOR SEQ ID NO: 9:

(i) SEQUENCE CHARACTERISTICS:
(A) LENGTH: 462
(B) TYPE: nucleic acid
(C) STRANDEDNESS: single
(D) TOPOLOGY: linear (ii) MOLECULE TYPE: cDNA
(A) DESCRIPTION: IL-4/T13D[R121D/Y124D]

(iii) HYPOTHETICAL: no (iv) ANTI-SENSE: no (xi) SEQUENCE DESCRIPTION: SEQ ID NO: 9:

```
ATG GGT CTC ACC TCC CAA CTG CTT CCC CCT CTG TTC TTC CTG CTA           45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC           90
Ala Cys Ala Gly Asn Phe Val His Gly His Lys Cys Asp Ile Thr
                20                  25                  30

TTA CAG GAG ATC ATC AAA GAT TTG AAC AGC CTC ACA GAG CAG AAG          135
Leu Gln Glu Ile Ile Lys Asp Leu Asn Ser Leu Thr Glu Gln Lys
                35                  40                  45

ACT CTG TGC ACC GAG TTG ACC GTA ACA GAC ATC TTT GCT GCC TCC          180
Thr Leu Cys Thr Glu Leu Thr Val Thr Asp Ile Phe Ala Ala Ser
                50                  55                  60

AAG AAC ACA ACT GAG AAG GAA ACC TTC TGC AGG GCT GCG ACT GTG          225
Lys Asn Thr Thr Glu Lys Glu Thr Phe Cys Arg Ala Ala Thr Val
                65                  70                  75

CTC CGG CAG TTC TAC AGC CAC CAT GAG AAG GAC ACT CGC TGC CTG          270
Leu Arg Gln Phe Tyr Ser His His Glu Lys Asp Thr Arg Cys Leu
                80                  85                  90

GGT GCG ACT GCA CAG CAG TTC CAC AGG CAC AAG CAG CTG ATC CGA          315
Gly Ala Thr Ala Gln Gln Phe His Arg His Lys Gln Leu Ile Arg
                95                  100                 105

TTC CTG AAA CGG CTC GAC AGG AAC CTC TGG GGC CTG GCG GGC TTG          360
Phe Leu Lys Arg Leu Asp Arg Asn Leu Trp Gly Leu Ala Gly Leu
                110                 115                 120

AAT TCC TGT CCT GTG AAG GAA GCC AAC CAG AGT ACG TTG GAA AAC          405
Asn Ser Cys Pro Val Lys Glu Ala Asn Gln Ser Thr Leu Glu Asn
                125                 130                 135

TTC TTG GAA AGG CTA AAG ACG ATC ATG GAC GAG AAA GAC TCA AAG          450
Phe Leu Glu Arg Leu Lys Thr Ile Met Asp Glu Lys Asp Ser Lys
                140                 145                 150

TGT TCG AGC TAG                                                      462
Cys Ser Ser End
```

We claim:

1. A recombinant human IL-4 mutein numbered in accordance with wild-type IL-4 wherein said mutein comprises at least one amino acid substitution selected from the group consisting of substitutions at positions 13, 16, 81 and 89 nof said wild-type IL-4, and whereby said mutein binds to the IL-4Rα receptor with at least greater affinity than native IL-4.

2. The recombinant human IL-4 mutein of claim 1, wherein said substitution at position 13 is Thr to Asp.

3. The recombinant human IL-4 mutein of claim 1 encoded by the amino acid sequence of SEQ ID NO: 8.

4. The recombinant human IL-4 mutein of claim 1 wherein said substitution at position 16 is serine to alanine.

5. The recombinant human IL-4 mutein of claim 1 wherein said substitution at position 16 is serine to aspartate.

6. The recombinant human IL-4 mutein of claim 1 wherein said substitution at position 16 is serine to histidine.

7. The recombinant human IL-4 mutein of claim 1 wherein said substitution at position 16 is serine to isoleucine.

8. The recombinant human IL-4 mutein of claim 1 wherein said substitution at position 16 is serine to leucine.

9. The recombinant human IL-4 mutein of claim 1 wherein said substitution at position 16 is serine to glutamine.

10. The recombinant human IL-4 mutein of claim 1 wherein said substitution at position 16 is serine to arginine.

11. The recombinant human IL-4 mutein of claim 1 wherein said substitution at position 16 is serine to threonine.

12. The recombinant human IL-4 mutein of claim 1 wherein said substitution at position 16 is serine to valine.

13. The recombinant human IL-4 mutein of claim 1 wherein said substitution at position 16 is serine to tyrosine.

14. The recombinant human IL-4 mutein of claim 1 wherein said substitution at position 81 is arginine to lysine.

15. The recombinant human IL-4 mutein of claim 1 wherein said substitution at position 89 is asparagine to isoleucine.

16. A recombinant human IL-4 antagonist mutein numbered in accordance with wild-type IL-4 wherein said mutein comprises:

(a) substitutions R121D and Y124D in the D-helix of said wild-type IL-4; and (b) at least one amino acid substitution selected from the group consisting of substitutions at positions 13, 16, 81 and 89 of said wild-type IL-4, and whereby said mutein binds to the IL-4Rα receptor with at least greater affinity than native IL-4.

17. The recombinant human IL-4 antagonist mutein of claim 16 wherein said substitution at position 13 is Thr to Asp.

18. A pharmaceutical composition comprising the recombinant human IL-4 antagonist mutein of claim 16 in combination with a pharmaceutically acceptable carrier.

19. The recombinant human IL-4 antagonist mutein of claim 16 encoded by the amino acid sequence of SEQ ID NO: 9.

20. The recombinant human IL-4 mutein of claim 17 encoded by the DNA sequence of SEQ ID NO: 9 or a stably hybridizable variant thereof.

21. A pharmaceutical composition comprising the recombinant human IL-4 mutein of claim 1 in combination with a pharmaceutically acceptable carrier.

* * * * *